US009726641B2

(12) United States Patent
Bourgelas et al.

(10) Patent No.: US 9,726,641 B2
(45) Date of Patent: Aug. 8, 2017

(54) SYSTEM AND METHOD OF CORRECTING A NON-CONCENTRIC ULTRASONIC IRIS INSPECTION RESULT (71) Applicants: Tommy Bourgelas, Shannon (CA); Martin St-Laurent, Quebec (CA); Guillaume Painchaud-April, Quebec (CA)

(72) Inventors: Tommy Bourgelas, Shannon (CA); Martin St-Laurent, Quebec (CA); Guillaume Painchaud-April, Quebec (CA)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 467 days.

(21) Appl. No.: 14/478,412

(22) Filed: Sep. 5, 2014

(65) Prior Publication Data
US 2016/0069995 A1 Mar. 10, 2016

(51) Int. Cl.
G01S 15/06 (2006.01)
G01S 7/56 (2006.01)
G01N 29/24 (2006.01)
G01N 29/44 (2006.01)
G01N 29/04 (2006.01)
G01N 29/06 (2006.01)
G01N 29/07 (2006.01)

(52) U.S. Cl.
CPC ....... *G01N 29/043* (2013.01); *G01N 29/0645* (2013.01); *G01N 29/07* (2013.01); *G01N 2291/011* (2013.01); *G01N 2291/101* (2013.01); *G01N 2291/106* (2013.01); *G01N 2291/2636* (2013.01)

(58) Field of Classification Search
CPC ............. G01N 29/043; G01N 29/0645; G01N 229/01; G01N 229/2636; G01N 29/07; G01N 229/011; G01N 2291/106
USPC ............ 702/39, 42; 73/601, 622, 623, 866.5
See application file for complete search history.

(56) References Cited

U.S. PATENT DOCUMENTS

| 4,212,207 | A | * | 7/1980 | Conradi | G01B 17/02 73/623 |
| 4,597,294 | A | * | 7/1986 | Brill, III | F22B 37/003 376/252 |
| 4,757,716 | A | * | 7/1988 | Nottingham | F01D 21/003 73/623 |
| 4,856,337 | A | * | 8/1989 | Metala | G01N 27/902 324/220 |
| 4,955,235 | A | * | 9/1990 | Metala | G01N 27/902 324/226 |
| 5,063,780 | A | * | 11/1991 | Landry | G01N 29/27 702/39 |

(Continued)

*Primary Examiner* — Carol S Tsai
(74) *Attorney, Agent, or Firm* — C. Tricia Liu (57) ABSTRACT Disclosed is an ultrasonic IRIS inspection system and a method of providing automatically compensated concentric B-scans by means of curve-fitting the unadjusted tube boundaries from inspection data, and from the curve fitted theoretical circle, using non-linear regression analysis to determine an adjusted center. The off-center distance between the adjust center and the misaligned center is then used to produce concentric inspection result by compensating the unadjusted inspection result with the off-center distance.

19 Claims, 7 Drawing Sheets (56) References Cited

U.S. PATENT DOCUMENTS

| | | | | |
|---|---|---|---|---|
| 5,088,328 | A * | 2/1992 | John, Jr. | G01B 17/00 |
| | | | | 73/622 |
| 5,329,824 | A * | 7/1994 | Carapezza | G01N 29/265 |
| | | | | 73/866.5 |
| 5,377,237 | A * | 12/1994 | Richardson | G01N 29/043 |
| | | | | 376/245 |
| 6,041,861 | A * | 3/2000 | Mandal | E21B 47/0005 |
| | | | | 166/250.01 |
| 6,886,407 | B1 * | 5/2005 | Fredenberg | G01N 29/262 |
| | | | | 73/622 |
| 2004/0254258 | A1 * | 12/2004 | Horikoshi | C08G 75/08 |
| | | | | 523/102 |
| 2012/0109540 | A1 * | 5/2012 | Torichigai | G01N 29/041 |
| | | | | 702/39 |

* cited by examiner

SYSTEM AND METHOD OF CORRECTING A NON-CONCENTRIC ULTRASONIC IRIS INSPECTION RESULT

FIELD OF THE INVENTION

This invention relates to non-destructive testing and inspection systems (NDT/NDI), particularly to conducting internal rotating inspection system (IRIS) ultrasonic inspection of tubular test objects using a corrected display compensating for changes in probe centering.

BACKGROUND OF THE INVENTION

An internal rotating inspection system (IRIS) is an immersion ultrasonic non-destructive testing (NDT) system used to measure the wall thickness or inspect the wall conditions of tubular materials, in particular for, but not limited to, heat exchanger tubing and boilers. IRIS technology is often used to confirm and provide sizing of outside diameter (OD) or internal diameter (ID) defects, such as multiple pit clusters.

An IRIS C-scan view is a succession of IRIS B-scans representing one probe turn. The B-scan is alternatively represented in a cylindrical view, which puts more into evidence the importance of probe centering. While the IRIS probes detect OD and ID pitting relatively easily by means of the B-scan view, the screening of the multiple defects in a C-scan view is a tedious process, and can lead to missing defects as errors are inevitable.

The C-scan view offers a color-coded display of the local ID value or the OD value. However in practice, the centering of the IRIS probe is virtually never perfect, and, more than often, significantly off-centered. This has the effect of shifting the whole color spectrum of ID or OD C-scan views, and hiding the defects that may be pushed outside the effective color range for detection.

While OD pits can be easily represented in a C-scan view by means of a "wall thickness" C-scan, ID pits cannot use such compensation; therefore the identification of ID pits in a C-scan view is very much dependent on probe centering.

Moreover, IRIS probe centering dynamically changes several times, in random moments, during the inspection. As a result, a simple ID defect analysis cannot be done. Standard practice is to find the deepest defect, yet an analyst must select each and every defect, measure or estimate its depth, take notes, and find the deepest one. This is a tedious process as many as several hundred defects can be found in tubes.

Some existing probe-centering methods inside a tubular testing material are used in existing practice. U.S. Pat. No. 5,329,824 discloses a probe-centering method of using multiple bendable support legs that are pivotally connected at different points to an inspection device inside a tube. U.S. Pat. No. 4,597,294 discloses a probe positioning system inside a tube using an oscilloscope, cam lock assemblies, and a predetermined axial extent from a magnetic tape recorder. However these solutions to centering a probe are mechanical, and do not have the precision offered by software working directly with the IRIS probe.

Considering the background information above, a solution that automatically centers an IRIS probe for C-scans would be of great economic value. It would be possible to obtain the same inspection and analysis results with existing IRIS equipment and software, but more intuitively and in a much faster way. An analyst could instantly locate the deepest defects and speed up the analysis, once the color palette has been properly adjusted. This would allow huge time savings while increasing the probability of detection, and also add further confidence in the IRIS technology or system being sold by a manufacturer.

SUMMARY OF THE INVENTION

It is a general object of the present disclosure to provide an IRIS inspection system that automatically compensates for the centering change by means of a signal processor that would eliminate the need for probe centering in an IRIS turbine featuring a rotatable motor.

It is a further a general object of the present disclosure to automatically recognize an OD, ID, or both tube diameters from a single B-scan in order to detect its center, and artificially displace the whole B-scan data in order to realign the center to where it should be.

It is a further a general object of the present disclosure to apply the automatic B-scan data center correction in continuous mode, and independently from each B-scan data, in order to enable the construction of fully corrected ID and OD C-scan views.

DETAILED DESCRIPTION OF THE INVENTION

Figure 1:
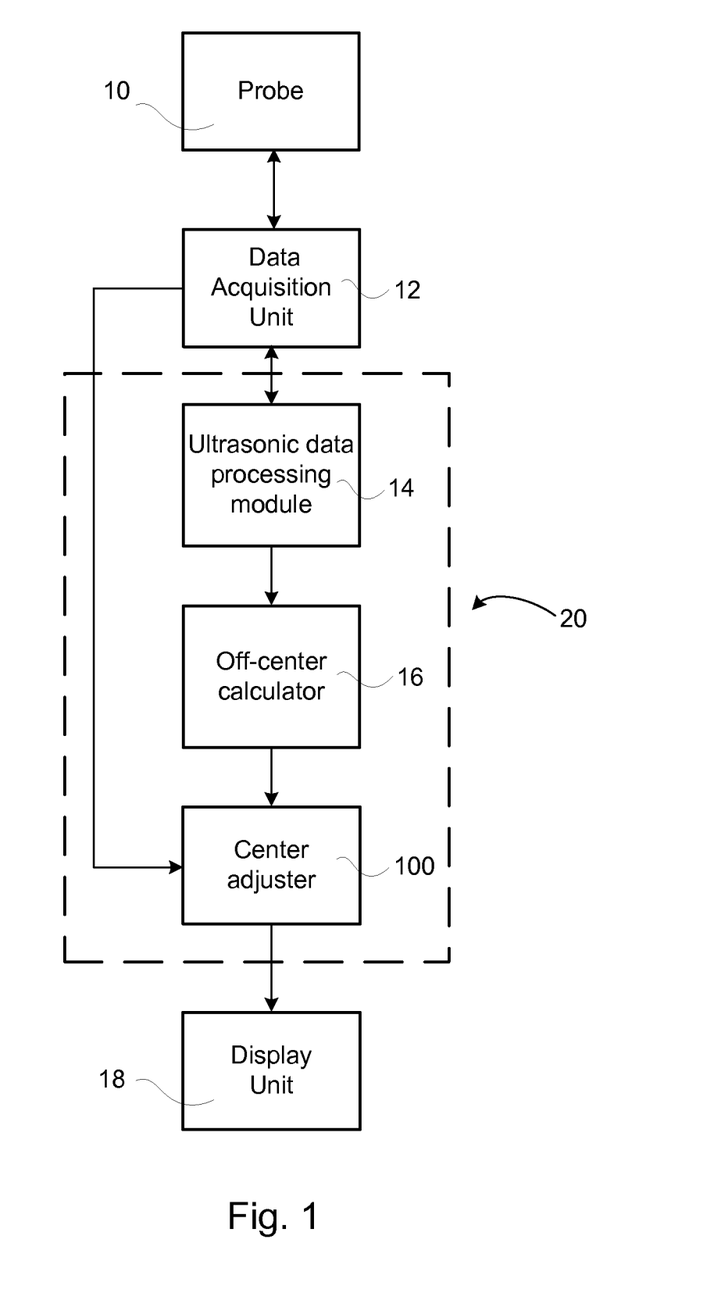
FIG. 1 is a schematic view of the IRIS inspection system with non-concentric correction according to the present disclosure.

Referring to FIG. 1, the apparatus of the present disclosure is comprised of a signal processor 20, which is further comprised of: an ultrasonic data processing module 14, an off-center calculator 16, and a center adjuster 100. Signal processor 20 is connected to a data acquisition unit 12, which has data connections to center adjuster 100 and to a probe 10, and is also connected to a display unit 18.

During a B-scan, probe 10 sends echo signals to data acquisition unit 12, which feeds data to signal processor 20, which further provides center location and correction from data processing module 14 and center adjuster 100.

Ultrasonic data processing module 14 determines the distance from the center location of a test object to a normal concentric B-scan reference center. If the center location is not aligned, off-center calculator 16 calculates a horizontal distance and a vertical distance from the normal concentric B-scan reference center. Center adjuster 100 then adjusts the horizontal distance and vertical distance values from the misaligned data center, so that the misaligned data center is aligned with the normal concentric B-scan reference center.

Continuing with FIG. 1, the adjusted distances from center adjuster 100 are sent to display unit 18, which obtains data from the corrected, centered view of the B-scan in order to build a fully corrected C-scan. This process is described in more detail in the following drawings and their descriptions.

Figures 2A, 2B, 2C, 2D:
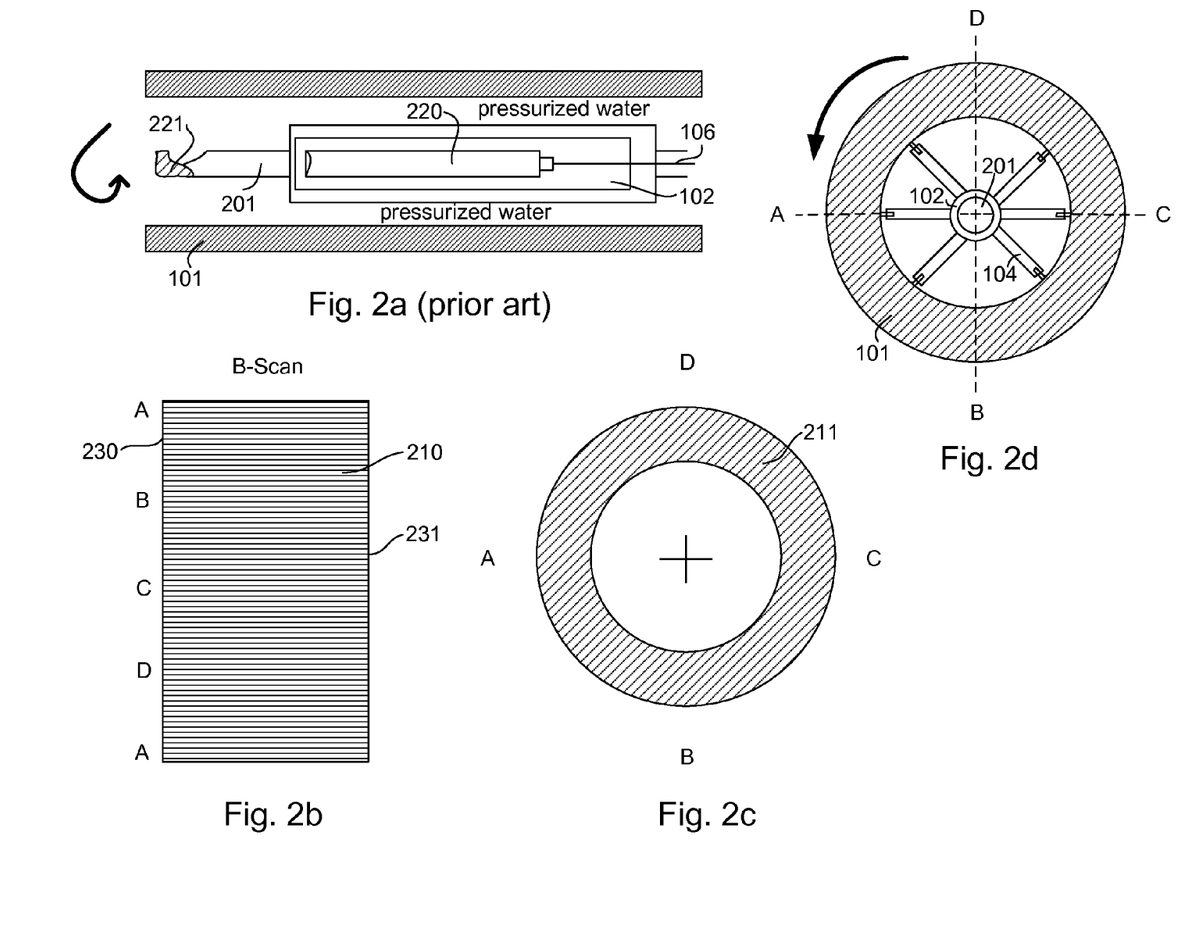
FIGS. 2a, 2b, 2c, and 2d illustrate an IRIS probe head inside a tubular material in a perfectly centered condition, with their associated B-scan and concentric B-scan views.

Referring to FIG. 2a, a probe assembly for an existing typical IRIS inspection is herein introduced for illustration purposes, exhibiting the concept of the "center" of a B-scan when it is aligned with the physical center of a tubular test object 101. Tubular test object 101 is connected by a cable 106, which provides an electrical connection, and fills the tubular test object with pressurized water. The pressurized water exits through a turbine rotatable mirror assembly 201. It's a common practice that an IRIS turbine 102 includes an immersion ultrasonic focalized transducer 220 that sends ultrasonic waves towards a turbine mirror 221. Ideally, the IRIS probe head inside tubular test object 101 is in a perfectly centered condition. The associated B-scan and concentric B-scan views associated with this perfectly centered condition are later directed by turbine mirror 221 to the surface of tubular test object 101. The ultrasonic wave is then reflected by the tubular test object's internal and external surfaces, returns into turbine mirror 221, and is received by immersion ultrasonic focalized transducer 220.

Referring to FIG. 2b, the resulting ultrasonic signals received from both the internal (ID) and external (OD) echoes of the surfaces are displayed in the Cartesian form of a B-scan view 210, featuring the time of flight measurement from an ID echo 230 and an OD echo 231, plotted against one complete turn (360°). For clarity, the positions around a full mirror rotation are represented as letters A, B, C, and D, referring to arbitrary references 90° apart. FIG. 2b shows the B-scan results in an ideal situation under which there is no non-concentric problem between the B-scan center and the physical ID or OD centers.

Referring to FIG. 2c, B-scan view 210 is also commonly represented in a polar pattern (a concentric B-scan 211). While it includes the same information as B-scan 210 under an ideal situation, the polar plot allows easier interpretation of the inspection results and easier visualization of eventual centering problems.

Referring to FIG. 2d, IRIS probe turbine 102 is considered perfectly centered when it is equally positioned inside tubular test object 101 through equal positioning of the centering arms 104 within turbine rotatable mirror assembly 201. When this occurs, B-scan view 210 displays ID echo 230 and OD echo 231 as straight lines in B-scan view 210, and results in a perfectly aligned pattern in concentric B-scan 211.

Figure 3A:
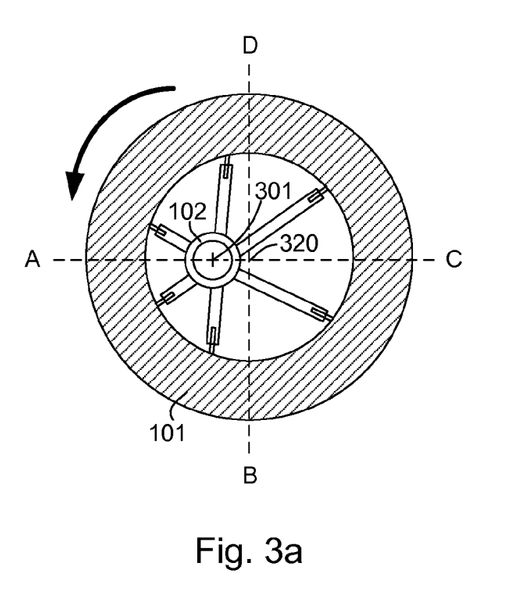
FIGS. 3a, 3b, 3c, and 3d illustrate an IRIS probe inside a tubular material in a non-centered condition, with their associated B-scan and concentric B-scan views.
Figure 3B:
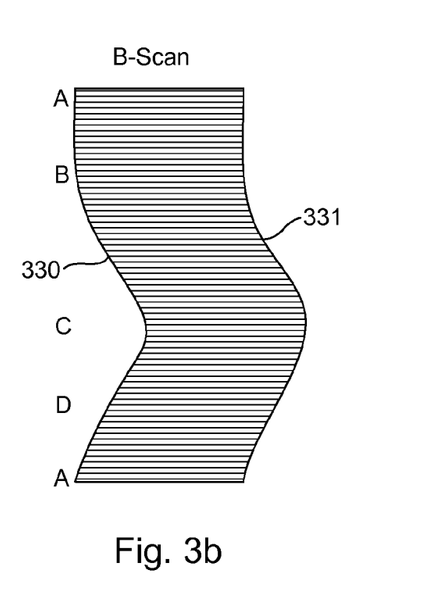

Referring to FIGS. 3a and 3b, IRIS turbine 102 is considered in a non-centered condition when it has a center of rotation 301 that is not perfectly aligned with a tubular probe center 320 of tubular test object 101. This condition is very common and could result from various causes during the inspection process.

Referring to FIG. 3b, the Cartesian form of a B-scan view from a non-centered condition produces a waved ID echo 330 and a waved OD echo 331, because the time of flight to a defect-free internal surface of tubular test object 101 is not constant across positions A, B, C, and D.

Figure 3C:
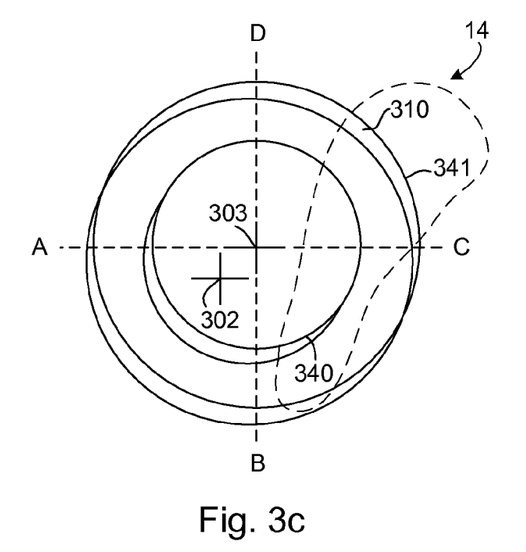

Referring to FIG. 3c, a concentric B-scan 310 from a non-centered condition also exhibits a misaligned data center 302 against a nominal reference center 303. Ultrasonic data processing module 14 (in FIG. 1) uses software pattern recognition in the misaligned concentric B-scan view to generate surface signals and their angle positions, and to locate the center of an ID echo 340 and also the center of an OD echo 341, which are the unadjusted inner and outer echoes, respectively. The center of ID echo 340 and alternatively, the center of OD echo 341 (in case ID echo 340 cannot be correlated) is used as a base to obtain adjustments of misaligned data center 302. How off-center calculator 16 uses the software pattern recognition from ultrasonic data processing module 14 is described in more details in FIGS. 5 and 6.

Figure 3D:
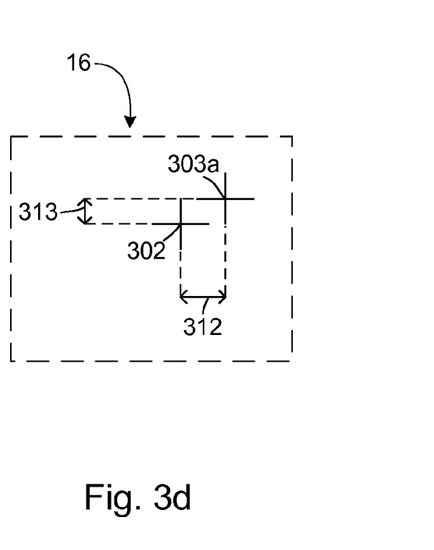

Referring to FIG. 3d, off-center calculator 16 compares the distance from an adjusted reference center 303a to misaligned data center 302, and calculates a horizontal distance 312 and a vertical distance 313 between the two centers. Off-center calculator 16 is described in more detail in FIGS. 7a and 7b.

Figure 4A:
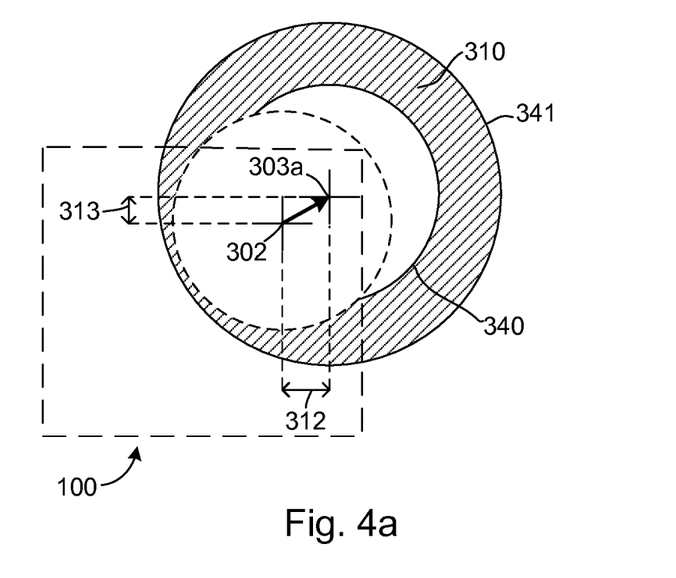
FIGS. 4a and 4b illustrate an IRIS probe head inside a tubular material in a non-centered condition being corrected by the present disclosure.

Referring to FIG. 4a, center adjuster 100 adjusts horizontal distance 312 and vertical distance 313 from misaligned data center 302, in order to obtain the view of adjusted reference center 303a.

Figure 4B:
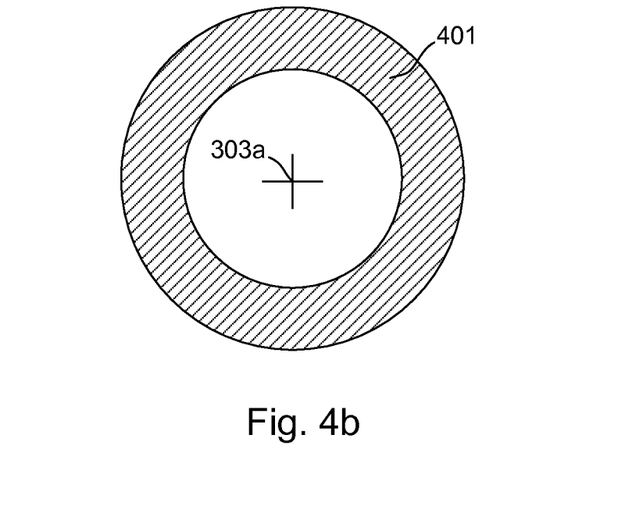

Referring to FIG. 4b, center adjuster 100 returns successive corrected B-scan data 401 with adjusted reference center 303a to display unit 18 in order to build a fully corrected C-scan, allowing easier and more rapid depth analysis of internal defects through color identification.

Figure 5:
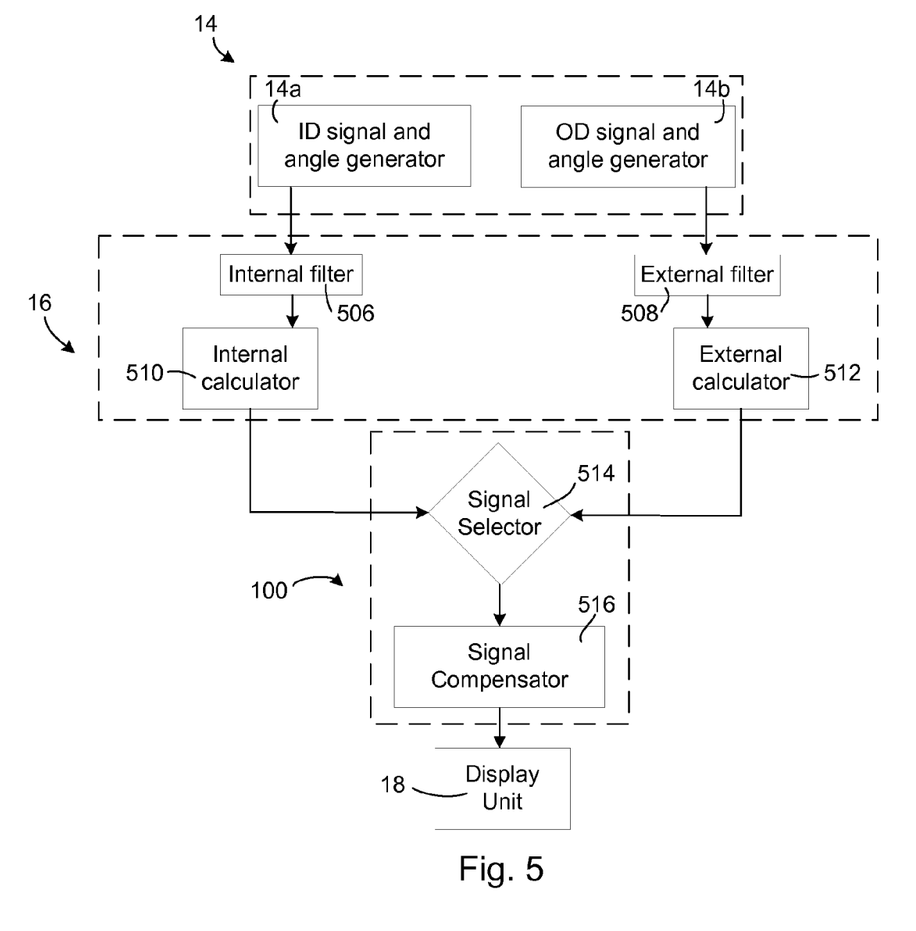
FIG. 5 is a flow chart of the components involved in compensating the measurement distances from an off-centered IRIS probe during an NDT/NDI test.

Reference is now made to FIG. 5, which shows the components of the present disclosure executing the process involved for returning successive corrected B-scan data 401 with adjusted reference center 303a to display unit 18. Ultrasonic data processing module 14 is further comprised of an internal surface (ID) signal and angle generator 14a and an external surface (OD) signal and angle generator 14b. Off-center calculator 16 is further comprised of an internal filter 506, an external filter 508, an internal calculator 510, and an external calculator 512. Center adjuster 100 is further comprised of a signal selector 514 and a signal compensator 516.

Figure 6:
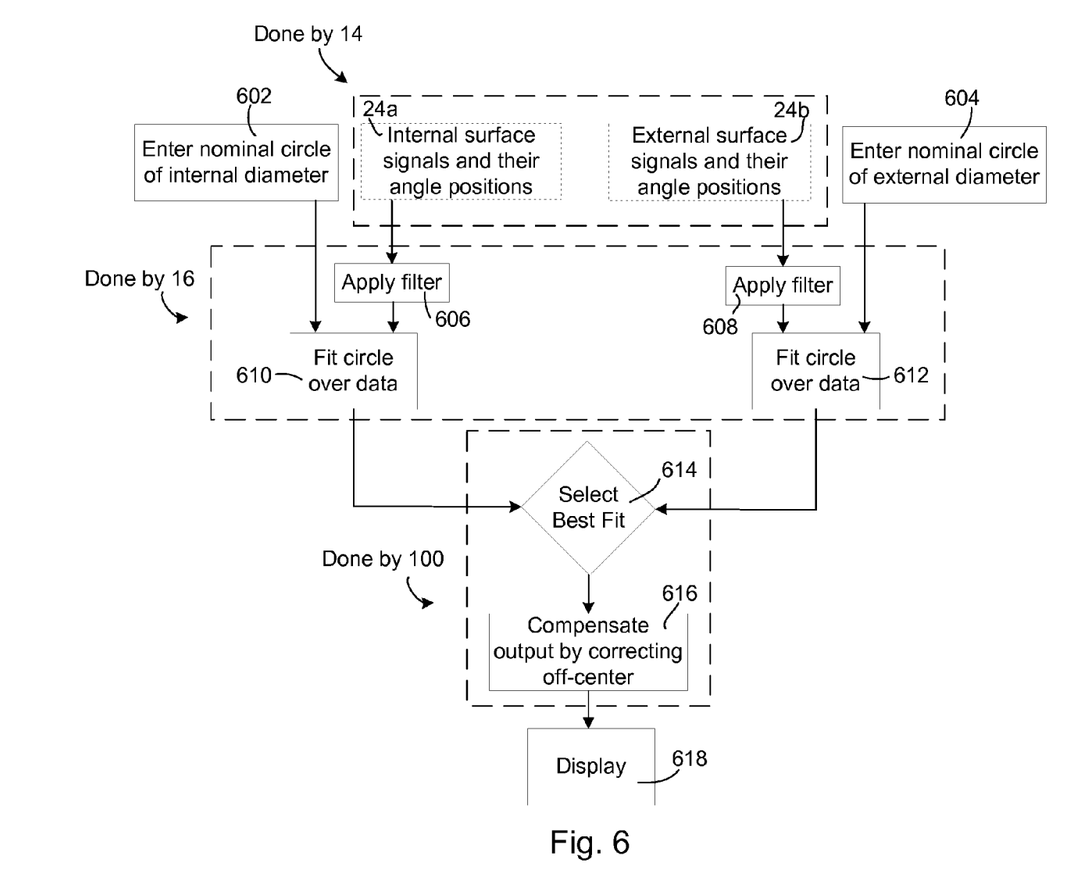
FIG. 6 is a flow chart of the steps involved in compensating the measurement distances from an off-centered IRIS probe during an NDT/NDI test.

Reference is now made to FIG. 6, which along with FIG. 5 show a flowchart of the steps involved for compensating horizontal distance 312 and vertical distance 313 from misaligned data center 302, and obtaining adjusted reference center 303a, using ID echo 340 and OD echo 341, which are misaligned or unadjusted data. First, an analyst enters a nominal circular shape of the diameter of tubular test object 101 for the internal diameter in step 602, and for the external diameter in step 604. Along with the tubular test object's internal surface signals and angle positions 24a and external surface signals and angle positions 24b (from internal surface signal and angle generator 14a and external surface signal and angle generator 14b in FIG. 5), these nominal circles are sent to off-center calculator 16.

Continuing with FIGS. 5 and 6, off-center calculator 16 first filters the signals from internal surface signal and angle generator 14a and an external surface signal and angle generator 14b. The purpose of the filters (506 and 508) is to remove signal data that is too high or too low for the nominal circles. More specifically, the filters determine all the radial boundary positions between misaligned data center 302 and adjusted reference center 303a that can be connected with a straight line, and that do not intersect with the border of tubular test object 101. Internal filter 506 filters internal surface signals and angle positions 24a in step 606, and external filter 508 filters external surface signals and angle positions 24b in step 608. The filtered signals are the data over which the nominal circles from step 602 and step 604 are fitted.

Figure 7A:
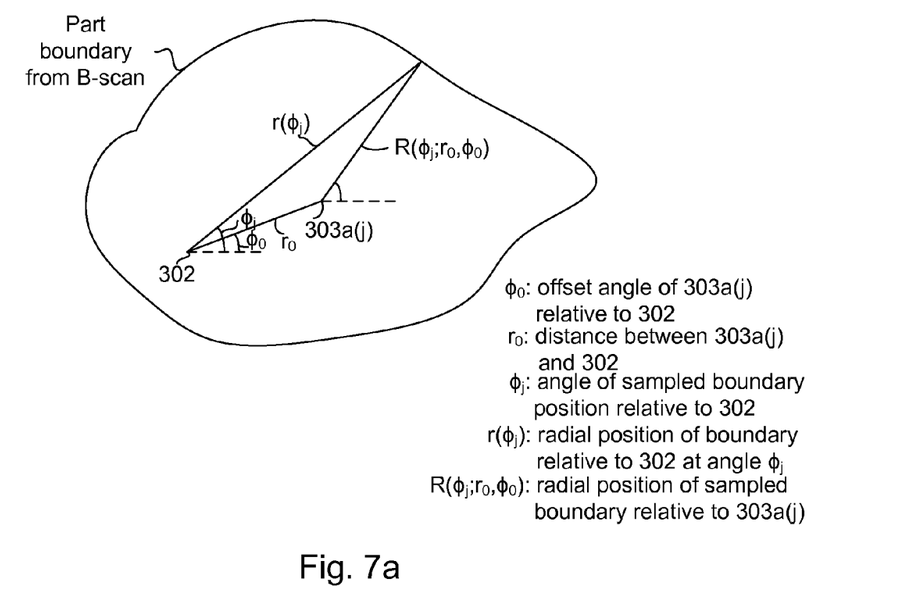
FIGS. 7a and 7b are detailed schematic views of the off-center calculator.

Referring to FIG. 7a, a part boundary computed from a B-scan is shown. The radial position of the part boundary relative to an assumed reference center 303a(j) can be calculated by Eq. 1 as follows:

$$R(\phi_j; r_0, \phi_0) = \sqrt{r^2(\phi_j) + r_0^2 - 2r(\phi_j) * r_0 * \cos(\phi_j - \phi_0)} \quad \text{Eq. 1}$$

where $R(\phi_j; r_0, \phi_0)$ is the radial position of the part boundary relative to assumed reference center 303a(j), the $\phi_j$, j=1 . . . J, are the J boundary position sample angles with respect to misaligned data center 302, $r_0$ is the distance between misaligned data center 302 and assumed reference center 303a(j), $\phi_0$ is the offset angle of assumed reference center 303a(j) with respect to misaligned data center 302, and $r(\phi_j)$ is the radial position of the part boundary relative to misaligned data center 302.

Figure 7B:
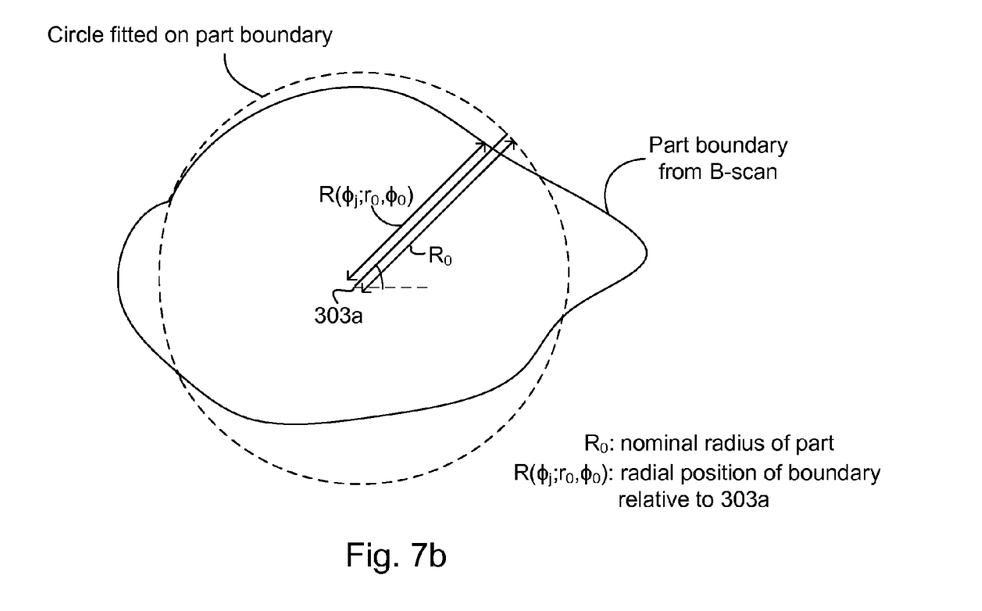

Referring to FIG. 7b, adjusted reference center 303a defined with respect to misaligned data center 302 through parameters $r_0$ and $\phi_0$ is optimized so that a circle of nominal radius $R_0$ best fits the filtered data. Then horizontal distance 312 and vertical distance 313 shown in FIG. 4a can be computed in order to obtain corrected centering data for center adjuster 100.

Referring back to FIGS. 5 and 6 and along with FIG. 7b, with adjusted reference center 303a and nominal radius $R_0$ defined, off-center calculator 16 then fits a theoretical circle over the filtered internal surface signals and angle positions 24a and external surface signals and angle positions 24b in order to obtain ID echo 340 and OD echo 341. In step 610, internal calculator 510 fits the circle over the internal signals and their angle positions of tubular test object 101; and in step 612 external calculator 610 fits the circle over the external signals.

Referring to FIG. 7b, a theoretical circle over the part boundary from a B-scan is shown. The method of obtaining the optimal position of adjusted reference center 303a, which thereafter becomes the adjusted reference center relative to misaligned data center 302, consists of adjusting the theoretical circle or radius $R_0$ over the filtered signals from step 610 for the internal signals and step 612 for the external signals with respect to an objective function. This can be performed by many mathematical methods, including non-linear regression analysis. One of the often used non-linear regression analysis is called "non-linear least squares" method. Using "non-linear least squares," an objective function $S(r_0, \phi_0)$ can be generated in Eq. 2 that sums the residual distances for all J boundary sample angles $\phi_j$, j=1 . . . J, from the circle of nominal radius $R_0$ and the observed boundary position from assumed reference center 303a (as calculated by Eq. 1):

$$S(r_0, \phi_0) = \sum_{j=1}^{J} [R(\phi_j; r_0, \phi_0) - R_0]^2 \quad \text{Eq. 2}$$

where $S(r_0, \phi_0)$ is an objective function to be minimized with respect to parameters $r_0$ and $\phi_0$, $\phi_j$ are the boundary sample angles with respect to the misaligned center 302, $r_0$ is the distance between misaligned data center 302 and assumed reference center 303a(j), $\phi_0$ is the offset angle of assumed reference center 303a relative to misaligned data center 302, and $R_0$ is the nominal radius of the part, either the part inner radius or the part outer radius. The non-linear least-squares method iteratively changes the parameters ($r_0$, $\phi_0$), starting from an initial guess, until the objective function $S(r_0, \phi_0)$ computed by Eq. 2 is minimal. Once the minimum value of $S(r_0, \phi_0)$ is reached, the assumed reference center is deemed the adjusted reference center 303a with optimal parameters ($r_0$, $\phi_0$). In other words, the adjusted reference center 303a is a special case of assumed reference center 303a(j) such that the sum of the squared differences between the part boundary position as observed from the assumed reference center and the circle of nominal radius $R_0$ whose origin is placed at the assumed reference center is minimal.

With the filtered radial position from Eq. 1, and the optimally adjusted reference center from Eq. 2, horizontal distance 312 and vertical distance 313 can now be calculated by off-center calculator 16 and sent to center adjuster 100.

Returning to FIGS. 5 and 6, center adjuster 100 evaluates the optimal radial position of the part boundary relative to adjusted reference center 303a, and implements it for centering the IRIS probe. In step 614, signal selector 514 compares the fittings from step 610 and step 612, and selects the lowest residual distance value, either from the internal or external signals. From the selected fit, the resulting offset radius and offset angle of the current scan are transformed from a polar to a Cartesian coordinate system, where horizontal distance 312 and vertical distance 313 are applied.

In step 616, signal compensator 516 transforms the surface signals and their angle positions of tubular test object 101 from a polar to a Cartesian coordinate system. Center adjuster 100 then compensates the X and Y coordinates of the output by the resulting offsets from step 614. In step 618, display unit 18 displays the compensated data as corrected B-scan data 401 shown in FIG. 4b.

While this invention has been described with reference to an exemplary embodiment, it will be understood that various changes may be made and equivalents may be substituted for elements thereof without departing from the spirit and scope of the invention. The embodiment described herein and the claims described hereof are not to be read restrictively unless there is clear and convincing evidence manifesting a certain exclusion, restriction, or disclaimer.

What is claimed is:

1. A non-destructive inspection apparatus with a probe assembly suitable for inspecting a test object of a shape of a tube having an inner surface and an outer surface, the probe attached to a centering roller and configured to travel along a nominal reference center inside and along the tube to inspect the tube during an inspection session, the inspection apparatus comprising:

a transducer residing within the probe assembly, configured to emit inspection energy to the tube and to receive corresponding echo signals;

a data acquisition unit electronically coupled with the transducer, configured to trigger and guide the inspection energy and receive the echo signals;

a data processing and display unit configured to process the echo signals to produce inspection data, firstly as an unadjusted inspection result, including an unadjusted inner boundary and/or an unadjusted outer boundary, the unadjusted inner and/or outer boundary is associated with a misaligned center, the data processing and display unit further comprising, an off-center calculator configured to curve-fit a theoretical inner and/or outer circle and an adjusted reference center based on the unadjusted inner and/or outer boundary, correspondingly, and the off-center calculator further configured to calculate an off-center distance between the misaligned center and the adjusted reference center, a center adjuster configured to produce an adjusted inspection result by compensating the unadjusted inspection result with the off-center distance.

2. The non-destructive inspection apparatus of claim 1 is an ultrasonic inspection apparatus and the inspection energy consists of ultrasonic pulses.

3. The non-destructive inspection apparatus of claim 2, wherein the transducer is a single element ultrasonic transducer.

4. The non-destructive inspection apparatus of claim 2, wherein the transducer is a multi-element or array element ultrasonic transducer.

5. The non-destructive inspection apparatus of claim 2, wherein the inspection data and the associated inspection results are presented as B-scans.

6. The non-destructive inspection apparatus of claim 2, wherein the inspection data and the associated inspection results are presented as C-scans.

7. The non-destructive inspection apparatus of claim 1, wherein the nominal reference center is known to and entered by an operator to the apparatus prior to the inspection session.

8. The non-destructive inspection apparatus of claim 7, wherein the nominal reference center is consistent with the center of the centering roller.

9. The non-destructive inspection apparatus of claim 1, wherein the data processing and display unit further comprising an ID signal and angle generator and OD signal and angle generator for generating the unadjusted inner boundary and the unadjusted outer boundary, respectively.

10. The non-destructive inspection apparatus of claim 9, wherein the off-center calculator further including an internal filter, an external filter, which filters out inspection data outside a predetermined threshold of an inner nominal circle or outer nominal circle, respectively.

11. The non-destructive inspection apparatus of claim 9, wherein the off-center calculator further comprising an internal calculator and an external calculator, each configured to conduct curve fitting to produce a theoretical inner circle and a theoretical outer circle, based on the unadjusted inner boundary and the unadjusted outer boundary, correspondingly.

12. The non-destructive inspection apparatus of claim 11, wherein the curve fitting is conducted by defining the inner or outer distance $$R(\phi_j; r_0, \phi_0) = \sqrt{r^2(\phi_j) + r_0^2 - 2r(\phi_j)*r_0*\cos(\phi_j - \phi_0)}$$

as from an assumed reference center ($303a(j)$) to the J boundary sample positions labelled $j=1 \ldots J$, wherein $R(\phi_j; r_0, \phi_0)$ is the radial position of the part boundary relative to assumed reference center $303a(j)$, $\phi_j$ is the angle of the $j^{th}$ boundary position relative to misaligned data center 302, $r_0$ is the distance between the misaligned data center 302 and assumed reference center $303a$, $\phi_0$ is the offset angle of assumed reference center $303a(j)$ relative to the misaligned data center 302, and $r(\phi_j)$ is the radial position of the part boundary relative to the misaligned data center 302.

13. The non-destructive inspection apparatus of claim 10, wherein the center adjuster further comprising a signal selector selecting a selected theoretical inner circle or the theoretical outer circle that is closest to the inner nominal circle or the outer nominal circle, respectively.

14. The non-destructive inspection apparatus of claim 10, wherein the selected theoretical inner or the selected theoretical outer circle is used to produce the adjusted reference center.

15. The non-destructive inspection apparatus of claim 14 employs non-linear regression analysis to deduce the adjusted reference center from the selected theoretical inner circle or the selected theoretical outer circle, with the nominal reference center as a non-linear regression starting point.

16. The non-destructive inspection apparatus of claim 15 is further configured to seek the adjusted reference center, a special case of the assumed reference center defined by parameters $r_0$ and $\phi_0$, such that objective function $S(r_0, \phi_0)$ is minimal, with $$S(r_0, \phi_0) = \sum_{j=1}^{J} [R(\phi_j; r_0, \phi_0) - R_0]^2$$

where $S(r_0, \phi_0)$ is an objective function to be minimized with respect to parameters $r_0$ and, $\phi_0$, $\phi_j$ are the J sampled angles of the boundary with respect to the misaligned data center with $j=1 \ldots J$, $r_0$ is the distance between the misaligned data center 302 and the assumed reference center $303a(j)$, $\phi_0$ is the offset angle of the assumed reference center $303a(j)$ relative to the misaligned data center 302, and $R_0$ is the nominal inner or outer radius of the test object.

17. A method of providing an adjusted inspection result correcting non-concentric inspection results of a non-destructive inspection apparatus, the apparatus including a probe assembly suitable for inspecting a test object of a shape of a tube having an inner surface and an outer surface, the probe attached to a centering roller and configured to travel along a nominal reference center inside and along the tube to inspect the tube during an inspection session, the method comprising the steps of:
emitting inspection energy to the tube and to receive corresponding response signals by using a transducer residing within the probe assembly;
regulating the inspection energy sent to the transducer and receiving the response signals from the transducer by using a data acquisition unit;
processing the response signals to produce inspection data, firstly as an unadjusted inspection result, including an unadjusted inner boundary and/or an unadjusted outer boundary, the unadjusted inner and/or outer boundary is associated with a misaligned center,
defining a theoretical inner and/or outer circle and an adjusted reference center by utilizing an off-center calculator to curve-fit the unadjusted inner and/or outer boundary, correspondingly,
calculating an off-center distance between the misaligned center and the adjusted reference center, and,
producing the adjusted inspection result by compensating the unadjusted inspection result with the off-center distance.

18. The method of claim 17 wherein the non-destructive inspection apparatus is an ultrasonic inspection apparatus and the inspection energy consists of ultrasonic pulses.

19. The method of claim 18 wherein defining the theoretical inner and/or outer circle is performed by curve-fitting the unadjusted inner and/or outer boundary, defining the adjusted reference center is performed by making non-linear regression analysis on the theoretical inner circle or the theoretical outer circle, with the nominal reference center as a non-linear regression starting point.

* * * * *